United States Patent
Ott et al.

(10) Patent No.: US 10,232,132 B2
(45) Date of Patent: Mar. 19, 2019

(54) CANNULA ADAPTERS

(71) Applicants: Douglas E. Ott, Macon, GA (US); Nathanial Tran, Apple Valley, MN (US)

(72) Inventors: Douglas E. Ott, Macon, GA (US); Nathanial Tran, Apple Valley, MN (US)

(73) Assignee: LEXON MEDICAL LLC, St. Paul, MN (US)

(*) Notice: Subject to any disclaimer, the term of this patent is extended or adjusted under 35 U.S.C. 154(b) by 807 days.

(21) Appl. No.: 13/694,680

(22) Filed: Dec. 20, 2012

(65) Prior Publication Data

US 2014/0180199 A1 Jun. 26, 2014

(51) Int. Cl.
*A61M 13/00* (2006.01)
*A61B 17/34* (2006.01)
*A61B 17/00* (2006.01)

(52) U.S. Cl.
CPC ....... *A61M 13/003* (2013.01); *A61B 17/3474* (2013.01); *A61B 2017/00486* (2013.01)

(58) Field of Classification Search
CPC .... A61M 13/00; A61M 13/003; A61M 31/00; A61M 2039/1077; A61B 17/34; A61B 17/3474; A61B 2017/00486; A61B 2017/34; A61B 17/341734; A61B 17/3421
USPC ............................................. 604/22, 26, 173
See application file for complete search history.

(56) References Cited

U.S. PATENT DOCUMENTS

| | | | | |
|---|---|---|---|---|
| 5,395,365 A | * | 3/1995 | Weiler | A61J 1/1406 128/DIG. 24 |
| 5,468,230 A | * | 11/1995 | Corn | A61M 25/02 604/174 |
| 2002/0183715 A1 | * | 12/2002 | Mantell | A61B 17/3496 604/506 |
| 2005/0212221 A1 | * | 9/2005 | Smith | F16J 3/00 277/628 |
| 2007/0088275 A1 | * | 4/2007 | Stearns | A61B 17/3421 604/164.01 |
| 2008/0086074 A1 | * | 4/2008 | Taylor | A61B 1/0008 604/26 |
| 2008/0139878 A1 | * | 6/2008 | Van Der Weiden | A61B 17/0401 600/37 |
| 2009/0270817 A1 | * | 10/2009 | Moreno | A61B 17/3462 604/264 |
| 2010/0210998 A1 | * | 8/2010 | Albrecht | A61B 17/3417 604/26 |
| 2011/0201883 A1 | * | 8/2011 | Cooper | A61B 17/3421 600/109 |
| 2014/0074015 A1 | * | 3/2014 | Mastri | A61B 17/3474 604/26 |

* cited by examiner

*Primary Examiner* — Imani Hayman
*Assistant Examiner* — Tiffany Legette-Thompson
(74) *Attorney, Agent, or Firm* — Johnson & Phung LLC

(57) ABSTRACT

A cannula adapter for converting a trocar insufflator into a two-phase or two-mode insufflation system. In the needle insufflation mode the insufflation gas flows through a trocar cannula, a cannula adapter and an insufflation needle before entering a body cavity and in the trocar insufflation mode gas flows directly into the body cavity from the trocar cannula. The cannula adapter although sealingly attachable to the trocar cannula during the needle insufflation mode is removable therefrom for a seamless transfer between the needle insufflation mode and the trocar insufflation mode.

8 Claims, 3 Drawing Sheets

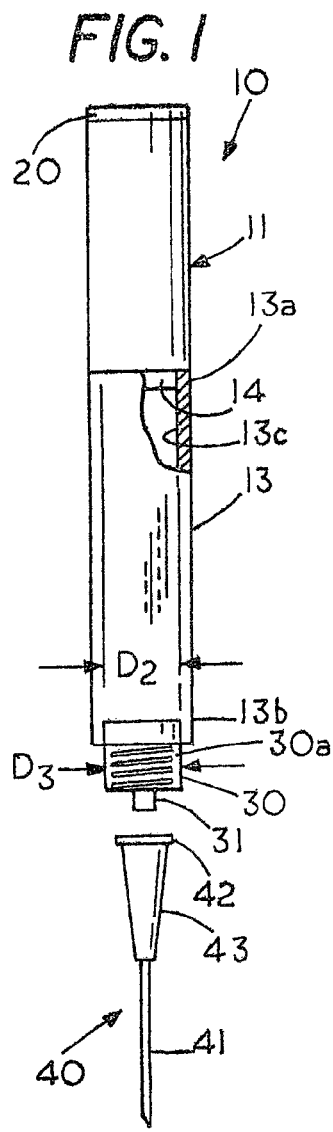
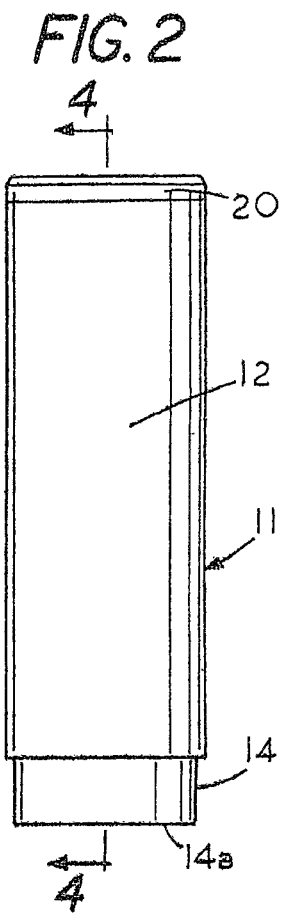
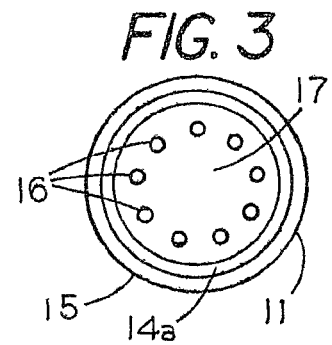
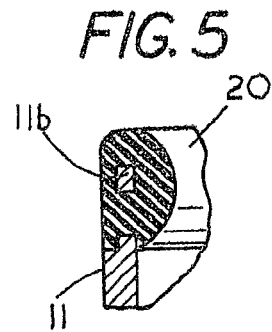
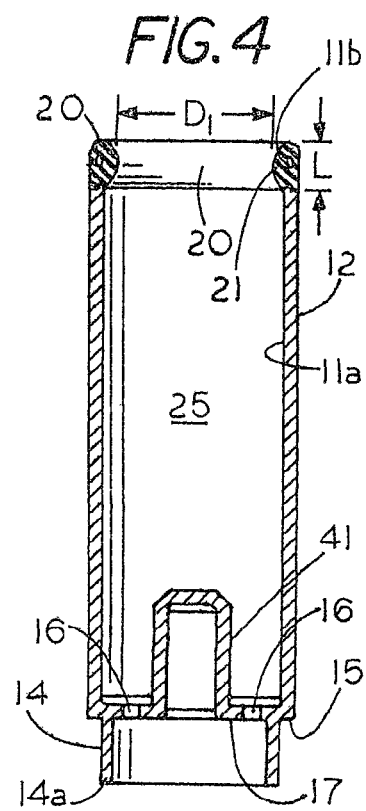

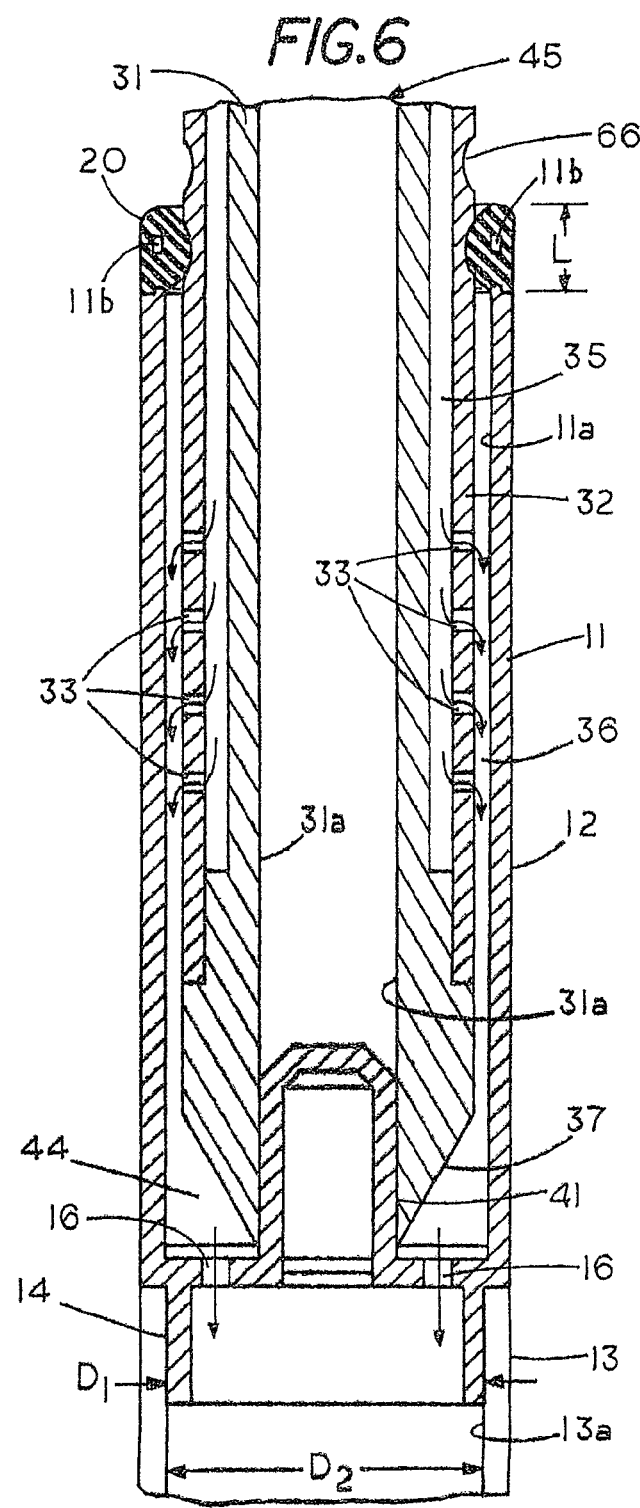

CANNULA ADAPTERS

CROSS REFERENCE TO RELATED APPLICATIONS

This application is a continuation in part of U.S. patent application Ser. No. 13/065,438 filed Mar. 22, 2011.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of a medical apparatus for humidifying or otherwise treating a gas from an insufflator during surgery is described in Douglas Ott et al. U.S. Pat. No. 5,411,474; 6,068,609 and 7,066,902. Briefly, an insufflation gas is heated and hydrated i.e. conditioned, before the gas is directed into a body cavity through a device such as a trocar. In order to hydrate the insufflation gas a charge of hydration fluid is typically injected into a device where the hydration fluid can humidify the insufflation gas and a heater can bring the insufflation gas to a temperature near body temperature. The conditioned insufflation gas is then sent to a trocar for injection into a body cavity of a patient.

One of the requirements for delivery of insufflation gas to a patient's body cavity is to maintain the proper flow of insufflation gas into the body cavity. Normally, gas flows from a high-pressure gas source, which is remote from the patient, through an insufflation device and finally into a trocar where the gas is injected into the patient's body cavity. Typically, the insufflation gas is stored in high-pressure containers and a pressure regulator reduces the pressure of the gas to a lower pressure. The low pressure gas is typically delivered to the trocar through an insufflation device containing a set of inline end connectors that couple the source of insufflation gas, the pressure regulator, the filter, the heater, or heater and hydrator to trocar to each other. During the insufflation process the insufflation gas, which is conditioned by filtering, heating and or hydrating before delivery flows through a number of inline end connectors, which are typically connected by flexible tubing.

The conditioned gas is then delivered to the patient through a trocar cannula that extends into the body cavity of a patient, however, in some cases it is preferred to begin the insufflation process with an insufflation needle rather than the larger trocar cannula since the insufflation needle has a smaller profile than the trocar cannula. In these cases one set of insufflation devices may be used with the insufflation needle and another set of insufflation devices may be used with the trocar. The present invention eliminates the need for separate insufflation systems.

SUMMARY OF THE INVENTION

A cannula adapter for converting a trocar insufflator into a two-phase or two-mode insufflation system comprising a needle insufflation mode and a trocar insufflation mode. In the needle insufflation mode the insufflation gas flows through a trocar cannula, a cannula adapter and an insufflation needle before entering a body cavity. The cannula adapter has a first end located in sealing engagement with the trocar cannula with the second end of the cannula adapter supporting an insufflation needle that flows insufflation gas into a body cavity. In the trocar insufflation mode one removes the cannula adapter and the insufflation needle from the insufflation system and inserts the trocar cannula directly into the body cavity. In this condition insufflation gas flows directly into the body cavity from the trocar cannula. The cannula adapter although sealingly attachable to the trocar cannula during the needle insufflation mode is preferably hand removable therefrom for a seamless transfer between the needle insufflation mode and the trocar insufflation mode.

BRIEF DESCRIPTION OF THE DRAWINGS

FIG. 1 is an exploded view showing an insufflation apparatus comprising a cannula adapter having one end of a tubing secured thereto with the other end of the tubing in sealing engagement with an insufflation needle;

FIG. 2 is a front view of the cannula adapter of FIG. 1 without the tubing attached thereto;

FIG. 3 is an end view of the cannula adapter of FIG. 1 without the tubing attached thereto;

FIG. 4 is a sectional view taken along lines 4-4 of FIG. 2;

FIG. 5 is an enlarged view of an annular resilient member for forming sealing engagement with a trocar cannula;

FIG. 6 shows a double lumen cannula in sealing engagement with the cannula adapter of FIG. 1;

DESCRIPTION OF THE PREFERRED EMBODIMENT

Figure 7:
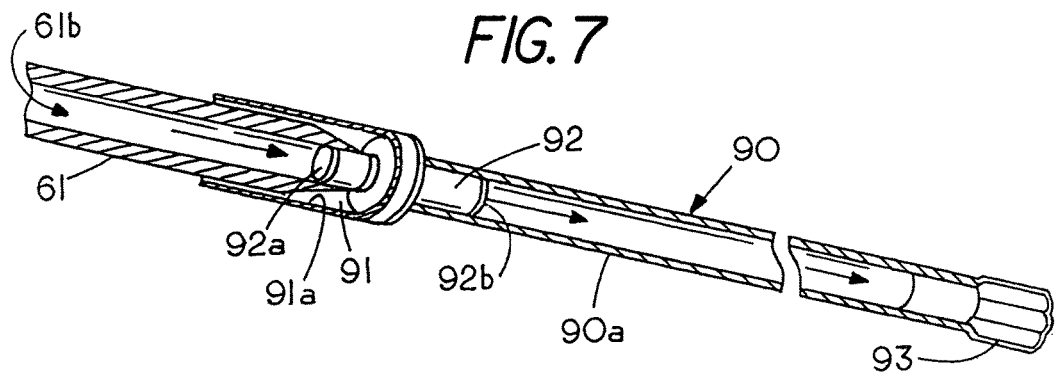
FIG. 7 is a sectional view of a single lumen cannula with a cannula adapter mounted in sealing engagement on the end of the single lumen cannula.

FIG. 1 is an exploded view showing a cannula attachable insufflation apparatus 10 comprising a cannula adapter 11, a tube 13, a fitting 30 and an insufflation needle 40. In the example shown the cannula adapter 11 comprises a rigid elongated tube 12 with one end for internal sealable, frictional engagement with an exterior surface of a trocar cannula and the other end of tube 12 having an annular band 14 for sealable, frictional engagement to a cylindrical interior surface 13c of a flexible tube 13. Sealingly and frictionally secured to the opposite end of tube 13 is a cylindrical fitting 30 having an outer cylindrical surface 30a in sealable frictional engagement with the cylindrical interior surface 13c of tubing 13. Fitting 30 comprises a collar having an internal fastener, such as female threads, for engagement with a hub 42 of an insufflation needle 40. The insufflation needle comprises an elongated tube 39 having an angled end for insertion through body tissue of a patient and a base 43 that connects hub 42 to tube 39.

In the example shown cannula adapter 11, insufflation needle 40, fitting 30 and tubing 13 are shown as a hand assembled insufflation apparatus with the individual components in sealable engagement with each other through frictional contact therebetween, however, other means of attachment may be used without departing from the spirit and scope of the invention. For example, in some case one may form the cannula adapter 11 the tubing 13, the fitting 30 and the insufflation needle 40 as one unit. In other cases one or more of the components may be removable. For example the fitting and the needle 40 may be removable to permit attachment of a different needle thereto. An example of suitable commercially available inflation needle is a verres needle although other needle inflation devices may be used with the system described herein.

FIG. 2 is an isolated front view of cannula adapter 11 comprising a rigid elongated tube 12 with a resilient band 20 on one end and an annular end 14a on the opposite end. Located proximate annular end 14a is annular band 14, which forms a tubing engaging surface for frictionally and sealingly supporting a flexible medical grade tubing or the like thereon. Although a rigid tube is shown a non-rigid tube may be used without departure from the spirit and scope of the invention.

FIG. 3 shows an end view of cannula adapter 11 revealing a set of gas ports 16 circumferentially spaced around end member 17 to permit flow of insufflation gas therethrough. An annular shoulder 15 forms a stop to limit insertion of tube 13 on band 14 as well as providing a depth guide as to the distance that a tube should be in frictional engagement with the surface 14 in order to prevent the insufflation gas pressure from dislodging or blowing the tube 13 free of cannula adapter 11 during the needle insufflation phase.

FIG. 4, which is a sectional view taken along lines 4-4 of FIG. 2 and FIG. 4, shows a sectional view of cannula adapter 11 taken along lines 4-4 of FIG. 2 revealing a cylindrical chamber 25 for receiving a trocar cannula. One end of cannula adapter 11 includes an internal dome shaped resilient band 20 that is supported by ribs 11b (FIG. 5) that extend from housing 12.

FIG. 6 shows a sectional view of cannula adapter 11 having one end in frictional, sealing engagement with a double lumen cannula 45 and the other end in frictional, sealing engagement with tubing 13. In the example shown in FIG. 6 the cannula adapter 11 comprises a hollow elongated rigid member 12 having an annular shoulder or band 14 on one end for frictional, sealing engagement with an interior surface 13c of inflation tube 13 with the diameter $D_1$ of resilient band 14 such that it forms frictional, sealing engagement through an interference fit with the interior cylindrical surface 13a (diameter $D_2$) to prevent the inflation tube 13 from becoming dislodged during the needle insufflation mode. The other end of cannula adapter includes 11 an internal resilient member 20 having a dome shape that is shapingly and frictionally mateable with the anti-removal annular serrations 66 on the exterior surface of cannula 45 to retain the cannula adapter 11 on the cannula 45 during the needle insufflation mode.

In the example shown the resilient band extends a distance L with the distance L such that the resilient band 20 can form frictional and shape mateable engagement over an extended cylindrical region of the trocar cannula 45 to maintain the cannula adapter 11 on the cannula 45 during a needle insufflation mode, yet allows the cannula adapter 11 to be quickly removed by medical persons when insufflation is switched from the needle insufflation mode to the trocar insufflation mode.

Extending upward from base 17 of cannula adapter 11 is a cylindrical post or locator 23 having an outer cylindrical surface 41 that is alignable with a central passage in a trocar cannula 45 to hold the trocar cannula 45 in axial alignment with the cannula adapter 11 as insufflation gas flows thorough gas ports 16 in end plate 17. Maintaining axial alignment between the cannula adapter 11 and the cannula 45 inhibits and prevents leakage therebetween during the needle insufflation phase since it limits movement of the seal 20 with respect to the trocar cannula 45.

FIG. 6 shows that the double lumen cannula 45 having an inner cylindrical wall 31 and an outer cylindrical wall 32 that coact to form an annular insufflation gas flow passage 35 therebetween. The resilient band 20 is shown located in sealing and shape mateable engagement with an anti-removal annular serrations 66 that extend around cannula 45. Although the band 20 and the anti-removal annular serrations 66 form shape mateable engagement as well as an interference fit the resilient band 20 the engagement pressure therebetween is such that one can with hand pressure slide the cannula adapter 11 onto or off the cannula 45. Once the cannula adapter 11 is in position the resilient force of band 20 forms sealing engagement between the cannula 45 and the adapter 11 to prevent the cannula from being dislodged from trocar cannula 45 as insufflation gas flows through trocar cannula 45 and into an insufflation needle, which is located downstream of the cannula adapter 11.

FIG. 6 shows cannula 45 contains a conical tapered end 37, which extends around post 23, with the inner cylindrical cannula surface 31a in locating engagement with the external cylindrical wall 41 of post 23 to maintain the cannula adapter 11 and the cannula 45 in axial alignment with each other to facilitate and retain sealing engagement between cannula 45 and cannula adapter 11.

FIG. 6 shows a set of flow arrows that illustrate how insufflation gas flows during the needle insufflation phase. More specifically, the insufflation gas flows into an annular chamber 35, radially outward through gas ports 33 and into a further annular chamber 36 located between the outer wall 32 of trocar cannula 45 and the internal cylindrical wall 11a of cannula adapter 11. The insufflation gas then flows through tube 13, fitting 30 and is discharged through insufflation needle 40.

Figure 9:
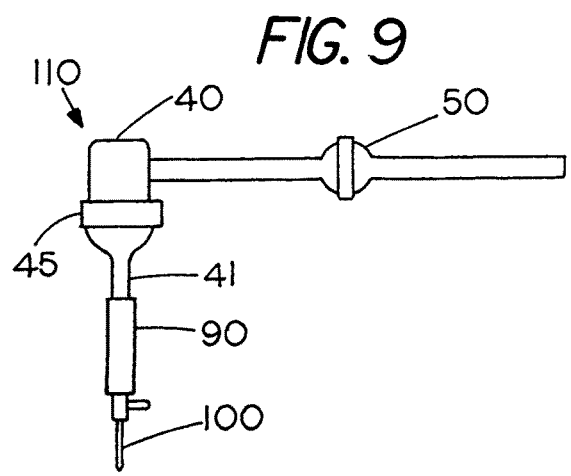
FIG. 9 is a front view of a two-phase insufflation apparatus in a needle inflation mode.

FIG. 7 shows a sectional view of a cannula adapter 90 attached to a single lumen cannula 61 and FIG. 9 shows a dual mode insufflation apparatus 110 with the cannula adapter 90. In the example shown in FIG. 7 the cannula adapter 90 is frictionally mounted on the distal end of trocar cannula 61 with a frictional, fluid seal formed between the engaging surfaces of the cannula adapter 90 and the cannula 61. Insufflation adapter 90 allows one to use the insufflation apparatus 40 (FIG. 9) in two different insufflation modes. In the trocar cannula inflation mode the cannula 61 directs insufflation gas directly into the body cavity through side ports on the cannula. In the needle insufflation mode the cannula directs the insufflation gas into the body cavity through an insufflation needle, which is temporarily attached to the cannula 41 through cannula adapter 90.

FIG. 7 shows a sectional view of the cannula adapter 90 comprising an elongated tube 90a having a first end with an annular member or sleeve 91 that fits over the distal end of the cannula 61 and a second end having a sleeve or connector 93 forming sealing attachment to an insufflation needle or the like. Located partially in one end of adapter 90 is a hollow plug or post 92 having one end extending into tube 90a and the other end into the distal end of cannula 61. The outside cylindrical surface of portion of plug 62, which extends into tube 90a, forms a fluid seal between adapter 90a and cannula 61. Plug 92 may be made from a resilient material to enable the resilience of the plug to form a pressure seal although other methods of sealing plug 92 to tube 90a may be used. The plug 92 includes a fluid passage 92a extending therethrough that allows insufflation gas to flow from cannula lumen 61b into adapter 90 and from there to an insufflation needle or the like attached thereto. The arrows indicate the direction of flow through the cannula 61, the plug 92 and the cannula adapter 90.

To prevent leakage of insufflation fluids the outside diameter of the plug 92 is such that it forms a snug fit with the cylindrical interior surfaces of cannula 61. If the cannula includes side ports for introduction of insufflation gas the annular sleeve 91 is of sufficient length to cover the side ports on the cannula to prevent flow therepast. To prevent leakage of fluid from the side ports of the cannula annular sleeve 61 the adapter sleeve 91a should form a snug fit, i.e. an interference fit, with the outer surface of the cannula 61. If desired a resilient material may be included on the inside surface of annular sleeve 91 with the interior surface of sleeve 91 forming a slight interference fit with the outside surface of the cannula 61. As an alternate sleeve 91 may be made from a resilient material to allow a snug leak proof connection to be formed with the distal end of the cannula. Thus the adapter 90 allows one to seal lateral ports on the cannula to prevent flow therethrough when the cannula adapter 90 is in use.

The distal end of adapter 90 includes a fitting 93 suitable for attachment to conventional insufflation needles, for example a verres needle. Fitting 93 may comprise a Leur fitting or the like to enable coupling with existing insufflation needles. With the insufflation apparatus 110 as described herein one has the option of using needle insufflation, which is smaller than the trocar, to initiate insufflation and when the initial needle insufflation is completed one can convert from a needle insufflation mode to a trocar insufflation mode by merely removing the adapter 90 and the insufflation needle from the end of cannula 61. The cannula 61 can then be used for direct insufflation of the body cavity of a patient. Thus, the cannula adapter 90 eliminates the need for a separate insufflation apparatus for trocar insufflation and needle insufflation since the trocar insufflation apparatus can be used during needle insufflation.

Figure 8:
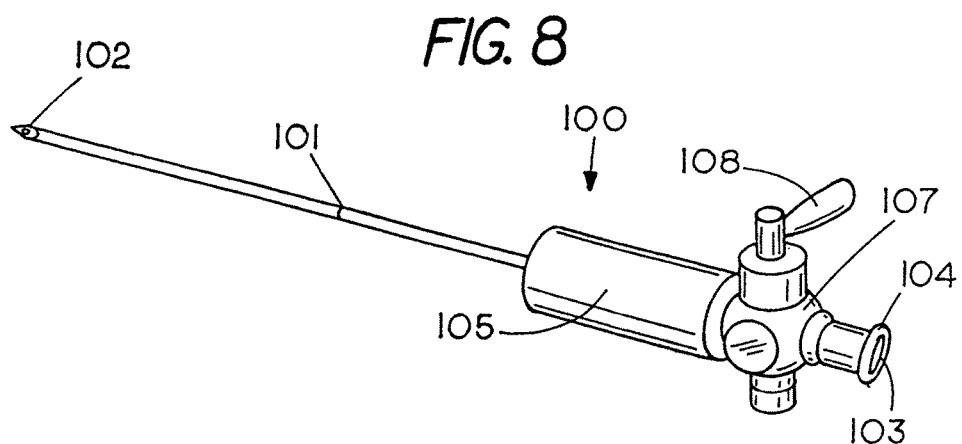
FIG. 8 is a perspective view of an insufflation needle and control valve.

FIG. 8 shows an example of a typical insufflation needle 100 for initial delivery of an insufflation gas to a body cavity. Insufflation needle 100 contains an elongated tube 101 with a pointed end 102 for piercing through body tissue and into a body cavity to enable one to begin the process of insufflating a body cavity. A housing 105 for grasping and manipulating the insufflation needle 100 supports one end of the elongated tube 101 and a valve 107 having a handle 105 to open and close the fluid path 103 through the tube 101, which extends from the other end of the housing 105. A fluid connector 104 extends from valve 107 to permit attachment of the insufflation needle 100 directly or indirectly to the cannula adapter 90 of FIG. 10. Connection to adapter 90 may be made through frictional engagement of connector 104 with connector 93 although other types of connections may be used for example, threaded or locking connectors.

FIG. 9 shows components of an insufflation apparatus 110 in an assembled ready to use state. In the assembled condition a fluid stabilizer 50 extends laterally from trocar 45 and the cannula adapter 90 connects to the cannula 41 of the trocar 45. The insufflation needle 100 extends outward from the adapter 90 to enable one to insufflating a body cavity from the insufflation gas delivered to fluid stabilizer 50. In this example the obturator has been removed since an inflation needle will be used to imitate the tissue piercing proximate the body cavity.

Insufflation apparatus 110 enables a user to insufflate a body cavity through either an insufflation needle or a trocar as well as to make an on-the-go change between the needle insufflation mode and a trocar insufflation mode. For example, insufflation needle 100 may be used for initial insufflation of the body cavity. When one needs to use the trocar to contain the instruments and maintain insufflation one can merely disconnect and remove the insufflation needle 100 and cannula adapter 90 from cannula 41. One can then insert cannula 41 directly into the body cavity without having to replace upstream devices. Not only can time be saved but also the use of separate insufflation apparatus for both the insufflation needle and the trocar is eliminated since the same fluid stabilizer and trocar can be used with trocar insufflation as well as needle insufflation. Thus, the method eliminates separate sterilizing or resterilization of the insufflation apparatus.

In the example shown all of the components such as the cannula adapter, the tubing, the fitting and the insufflation needle may be rigidly connected to each other so that the insufflation apparatus can be manipulated as a unit. In other cases only some of the components may be rigidly connected and others flexibly connected, for example one may want the insufflation needle to be separately manipulated from the trocar through use of a flexible tubing connected to the cannula adapter.

We claim:
1. A cannula adapter comprising:
a rigid tube having a chamber therein for receiving a trocar cannula;
an internal annular resilient dome-shaped cannula sealing member proximate a first end of the rigid tube, said dome-shaped cannula sealing member forming sealing engagement with an exterior surface of the trocar cannula to maintain the adapter on the cannula during a needle insufflation mode and to allow medical staff to easily remove the annular resilient dome-shaped cannula sealing member to switch to a trocar insufflation mode wherein insufflation is maintained through the cannula and a medical instrument is contained in the cannula;
an end member located on an opposite end of the first end of the rigid tube, said end member having an annular gas passage comprising a set of circumferentially positioned openings in said end member;
a cannula alignment member extending into the chamber with the cannula alignment member having an outer cylindrical surface that is alignable with an inner cylindrical sidewall in the trocar cannula to block an open end of the trocar cannula and hold the trocar cannula in axial alignment with the cannula adapter as insufflation gas flows through a sidewall of the trocar cannula and into the set of circumferentially positioned openings in the end member; and
an annular external sealable band with a stop located on the opposite end of the first end of the rigid tube said annular external sealable band forming an annular tubing engaging surface;
a flexible tubing frictionally and sealingly supported on said annular tubing engaging surface with said stop limiting insertion of the flexible tubing on the annular external sealable band and thus preventing the insufflation gas pressure from dislodging the flexible tube, said flexible tube for delivery of the insufflation gas therethrough to insufflate a body cavity.

2. The cannula adapter of claim 1 wherein said internal annular resilient dome-shaped cannula sealing member is supported by a set of ribs.

3. The cannula adapter of claim 1 wherein the internal annular resilient dome shaped cannula sealing member is deformable in a radial direction.

4. The cannula adapter of claim 1 including an insufflation needle secured to a second end of the flexible tubing.

5. The cannula adapter of claim 1 wherein the cannula alignment member comprises a cylindrical post.

6. The cannula adapter of claim 5 wherein the cylindrical post extends along a central axis of the rigid tube and the post is hollow.

7. A method of body cavity insufflation comprising the steps of:
- frictionally and sealingly attaching a first end of a rigid tube having a dome shaped sealing member supported by ribs onto an exterior surface of a cannula by shapingly mating said dome shaped sealing member onto an annular serration on said exterior surface of the cannula to retain the rigid tube on the cannula during a needle insufflation mode;
- attaching a one end of a flexible tubing having an insufflation needle on the opposite end of the flexible tubing around an exterior surface of an annular band of a second end of the rigid tube;
- inserting the insufflation needle through a body tissue and into a body cavity of a patient;
- directing an insufflating gas into an annular chamber and through a set of radial ports into a further annular chamber and into a set of circumferentially spaced gas ports located in an end plate of the rigid tube, into the insufflation needle and into a body cavity to initiate insufflation;
- removing the flexible tubing from the cannula after an initial insufflation to change from the needle insufflation mode to a trocar insufflation mode;
- inserting the cannula through a body wall of the patient without resterilization of the insufflation apparatus; and
- continuing insufflation of the body cavity through the cannula while using a medical instrument through the cannula.

8. The method of claim 7 including the step of concentrically aligning an open end of the cannula with a post in the rigid tube to thereby inhibit leakage of the insufflation gas.

* * * * *